US008722913B2

(12) United States Patent
Lang et al.

(10) Patent No.: US 8,722,913 B2
(45) Date of Patent: May 13, 2014

(54) METHOD FOR PRODUCING HIGHER SILANES

(75) Inventors: Juergen Erwin Lang, Karlsruhe (DE); Hartwig Rauleder, Rheinfelden (DE); Ekkehard Mueh, Rheinfelden (DE)

(73) Assignee: Evonik Degussa GmbH, Essen (DE)

( * ) Notice: Subject to any disclaimer, the term of this patent is extended or adjusted under 35 U.S.C. 154(b) by 1058 days.

(21) Appl. No.: 12/524,371

(22) PCT Filed: Dec. 20, 2007

(86) PCT No.: PCT/EP2007/064322
§ 371 (c)(1),
(2), (4) Date: Jul. 24, 2009

(87) PCT Pub. No.: WO2008/098640
PCT Pub. Date: Aug. 21, 2008

(65) Prior Publication Data
US 2010/0080746 A1  Apr. 1, 2010

(30) Foreign Application Priority Data
Feb. 14, 2007 (DE) .......................... 10 2007 007 874

(51) Int. Cl.
*C07F 7/12* (2006.01)
(52) U.S. Cl.
USPC .......................... 556/430; 556/452
(58) Field of Classification Search
USPC .......... 568/800, 700; 423/325, 341, 342, 349; 556/430, 452
See application file for complete search history.

(56) References Cited

U.S. PATENT DOCUMENTS

| | | | |
|---|---|---|---|
| 4,295,986 A * | 10/1981 | Gordon | 252/188.26 |
| 4,568,437 A | 2/1986 | Dickson, Jr. | |
| 4,830,890 A * | 5/1989 | Kanai | 427/255.39 |
| 4,923,687 A | 5/1990 | Schork et al. | |
| 4,950,373 A * | 8/1990 | Sundermeyer et al. | 204/164 |
| 5,026,533 A | 6/1991 | Matthes et al. | |
| 5,616,755 A | 4/1997 | Seiler et al. | |
| 5,654,459 A | 8/1997 | Kropfgans et al. | |
| 5,698,726 A | 12/1997 | Rauleder et al. | |
| 5,852,206 A | 12/1998 | Horn et al. | |
| 6,142,024 A | 11/2000 | Rauleder et al. | |
| 6,150,551 A | 11/2000 | Kropfgans et al. | |
| 6,177,584 B1 | 1/2001 | Loewenberg et al. | |
| 6,222,056 B1 | 4/2001 | Bade et al. | |
| 6,291,698 B1 | 9/2001 | Bade et al. | |
| 6,372,190 B1 | 4/2002 | Zehe et al. | |
| 6,585,941 B2 | 7/2003 | Zehe et al. | |
| 6,680,038 B2 | 1/2004 | Rauleder et al. | |
| 6,727,375 B2 | 4/2004 | Steding et al. | |
| 7,204,963 B2 | 4/2007 | Rauleder et al. | |
| 7,410,914 B2 | 8/2008 | Kuehnle et al. | |
| 7,507,850 B2 | 3/2009 | Muh et al. | |
| 8,038,961 B2 | 10/2011 | Sonnenschein et al. | |
| 8,105,564 B2 | 1/2012 | Sonnenschein et al. | |
| 2004/0224089 A1 | 11/2004 | Singh et al. | |
| 2004/0259386 A1 | 12/2004 | Tanaka et al. | |
| 2004/0266176 A1 | 12/2004 | Tanaka et al. | |
| 2004/0266177 A1 | 12/2004 | Tanaka et al. | |
| 2007/0240632 A1 | 10/2007 | Singh et al. | |
| 2008/0102218 A1 | 5/2008 | Comita et al. | |
| 2008/0197014 A1 | 8/2008 | Lang et al. | |
| 2008/0283972 A1 | 11/2008 | Muh et al. | |
| 2008/0289690 A1 | 11/2008 | Sonnenschein et al. | |
| 2009/0020413 A1 | 1/2009 | Popp et al. | |
| 2009/0259063 A1 | 10/2009 | Lang et al. | |
| 2010/0266489 A1 | 10/2010 | Rauleder et al. | |
| 2010/0270296 A1 | 10/2010 | Rauleder et al. | |
| 2010/0274028 A1 | 10/2010 | Mueh et al. | |
| 2010/0278706 A1 | 11/2010 | Mueh et al. | |
| 2010/0296994 A1 | 11/2010 | Rauleder et al. | |
| 2010/0320072 A1 | 12/2010 | Schwarz et al. | |
| 2012/0177557 A1 | 7/2012 | Rauleder et al. | |
| 2012/0183464 A1 | 7/2012 | Mueh et al. | |
| 2012/0195804 A1 | 8/2012 | Lang et al. | |
| 2012/0214005 A1 | 8/2012 | Wieber et al. | |
| 2013/0043893 A1 | 2/2013 | Mueh et al. | |

FOREIGN PATENT DOCUMENTS

WO 2004 036631 4/2004
WO 2006 013129 2/2006

OTHER PUBLICATIONS

U.S. Appl. No. 12/812,857, filed Jul. 14, 2010, Mueh, et al.
U.S. Appl. No. 12/999,240, filed Dec. 15, 2010, Seliger, et al.
Gokhale, S. D. et al., "Synthesis of the Higher Silanes and Germanes", J. Inorg. Nucl. Chem., vol. 27, pp. 1911-1916 (1965) XP-002517112.
Spanier, E. J. et al., "The Conversion of Silane to Higher Silanes in a Silent Electric Discharge", Inorg. Chem., vol. 1, No. 2, pp. 432-433 (1962) XP-002517113.
U.S. Appl. No. 13/884,473, filed May 9, 2013, Mueh, et al.
U.S. Appl. No. 13/884,326, filed May 9, 2013, Mueh, et al.
U.S. Appl. No. 14/111,643, filed Oct. 14, 2013, Mueh, et al.
U.S. Appl. No. 13/985,477, filed Aug. 14, 2013, Mueh, et al.

* cited by examiner

*Primary Examiner* — Sudhakar Katakam
*Assistant Examiner* — Pancham Bakshi
(74) *Attorney, Agent, or Firm* — Oblon, Spivak, McClelland, Maier & Neustadt, L.L.P.

(57) ABSTRACT

The invention relates to a method for producing dimeric and/or trimeric silicon compounds, in particular silicon halogen compounds. The claimed method is also suitable for producing corresponding germanium compounds. The invention also relates to a device for carrying out said method to the use of the produced silicon compounds.

16 Claims, 1 Drawing Sheet

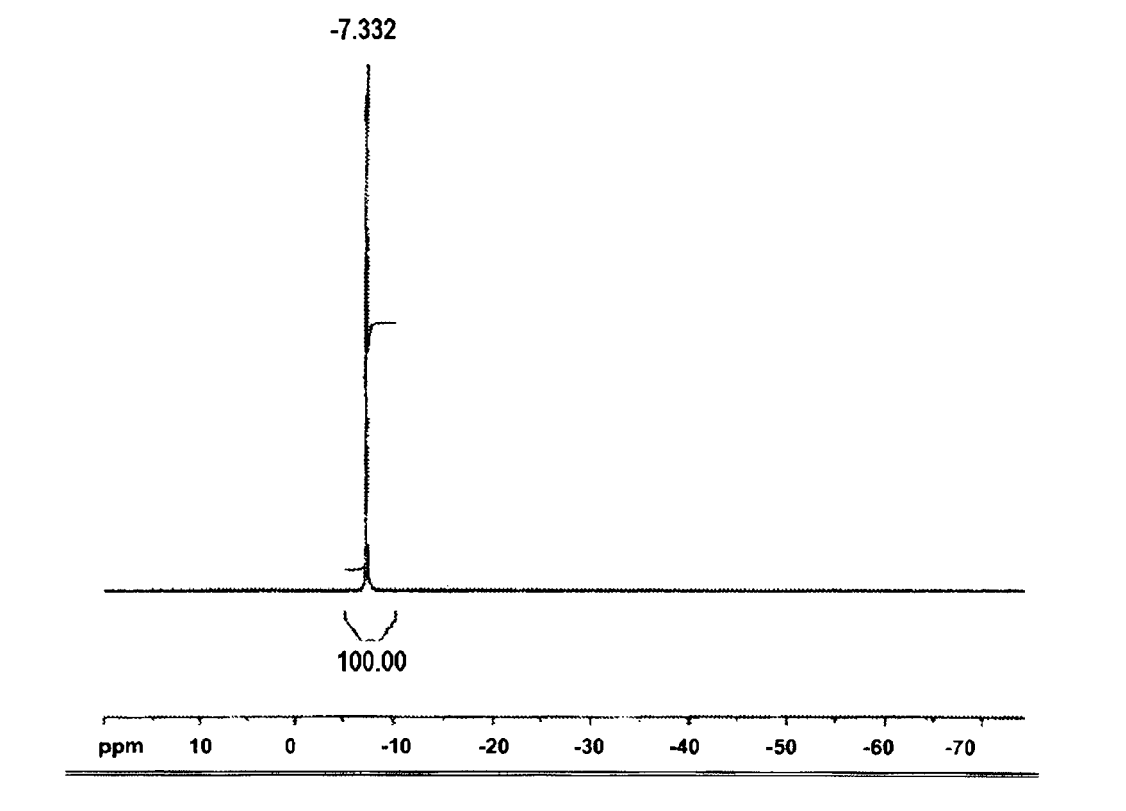

METHOD FOR PRODUCING HIGHER SILANES

CROSS REFERENCE TO RELATED APPLICATION

This application is a 371 of PCT/EP2007/064322, filed on Dec. 20, 2007, and claims priority to German Patent Application No. 10 2007 007 874.0, filed on Feb. 14, 2007.

The invention relates to a process for preparing dimeric and/or trimeric silicon compounds, especially silicon-halogen compounds. In addition, the process according to the invention is also suitable for preparing corresponding germanium compounds. The invention further relates to an apparatus for performing the process and to the use of the silicon compounds prepared.

Silicon compounds used in microelectronics, for example for producing high-purity silicon by means of epitaxy or silicon nitride (SiN), silicon oxide (SiO), silicon oxynitride (SiON), silicon oxycarbide (SiOC) or silicon carbide (SiC), have to meet particularly high demands on their purity. This is true especially in the case of production of thin layers of these materials. In the field of application mentioned, even contaminations of the starting compounds in the ppb to ppt range are troublesome. For example, hexachlorodisilane in the required purity is a sought-after starting compound in the field of electronics, in the semiconductor industry and in the pharmaceutical industry.

To prepare the high-purity compounds mentioned, silicon nitride, silicon oxide, silicon oxynitride, silicon oxycarbide or silicon carbide, especially layers of these compounds, hexachlorodisilane is converted by reaction with further nitrogen-, oxygen- or carbon-containing precursors. Hexachlorodisilane is also used to produce epitactic silicon layers, by means of low-temperature epitaxy.

Known prior art processes utilize, for preparation of halogen compounds of silicon, for example for preparation of hexachlorodisilane (disilicon hexachloride), the reaction of chlorine or hydrogen chloride with calcium silicide or else with copper silicide. A further process consists in the reaction of tetrachlorosilane (silicon tetrachloride) as it is passed over molten silicon (Gmelin, System No. 15, Part B, 1959, pages 658 to 659). A disadvantage of both processes is the chlorination, which takes place to an equal extent, of the impurities present in the calcium silicide and in the silicon, which are then entrained into the product. If the hexachlorodisilane is to be used in the production of semiconductors, these impurities are unacceptable.

According to the disclosure of German patent DE 1 142 848 from 1958, ultrahigh-purity hexachlorodisilane is obtained when gaseous silicochloroform is heated to 200 to 1000° C. in an electrode burner and the gas mixture obtained is cooled and condensed rapidly. To increase the efficiency, the silicochloroform is diluted with hydrogen or an inert gas before the reaction.

German patent DE 1 014 971 from 1953 relates to a process for preparing hexachlorodisilane, in which silicon tetrachloride is reacted with a porous silicon molding at elevated temperature, preferably at more than 1000° C., in a hot wall reactor.

DE-A 3 62 493 discloses a further process for preparing hexachlorodisilane. Here, hexachlorodisilane is prepared on the industrial scale by reacting silicon alloys or metallic silicon with chlorine using a vibration reactor at temperatures in the range from 100 to 500° C.

D. N. Andrejew (J. für praktische Chemie, Series 4. Vol. 23, 1964, pages 288 to 297) describes the reaction of silicon tetrachloride ($SiCl_4$) in the presence of hydrogen ($H_2$) under plasma conditions to give hexachlorodisilane ($Si_2Cl_6$) and higher chlorinated polysilanes. The reaction products are obtained as a mixture. A disadvantage of this process is that this product mixture is obtained in highly viscous to solid form and can therefore precipitate on the reactor wall. Likewise disclosed is the reaction of alkylsilanes such as methyltrichlorosilane (MTCS) in the presence of hydrogen in a plasma to give hexachlorodisilane and a multitude of undesired by-products. What is common to both embodiments is the disadvantageous additional requirement for hydrogen as a reducing agent.

WO 2006/125425 A1 relates to a two-stage process for preparing bulk silicon from halosilanes. In the first step, preferably halosilanes, such as fluoro- or chlorosilanes, are exposed to a plasma discharge in the presence of hydrogen. In the second stage which follows, the polysilane mixture obtained from the first stage is pyrolyzed to silicon at temperatures from 400° C., preferably from 700° C.

Features common to most of the processes mentioned are that they proceed at high temperatures and with considerable energy expenditure, require hydrogen as a reducing agent or lead to highly contaminated crude products with a multitude of by-products.

It is an object of the present invention to provide an economically viable process for preparing dimeric and/or trimeric silicon compounds on the industrial scale, which does not have the aforementioned disadvantages, and also an apparatus which is suitable especially for performing the process, and the use of the compounds prepared. The process should also be applicable to corresponding germanium compounds.

The object is achieved by the process according to the invention and the inventive apparatus according to the features of claims 1 and 14.

The process according to the invention divides into two process steps. In process step a), a nonthermal plasma treatment of a silicon compound of the general formula (IIa) is effected, optionally in the presence of one or further silicon compounds of the general formula (IIIa), which is especially a hydrogen-containing compound. According to the invention, the addition of hydrogen ($H_2$) can be dispensed with. Process step a) is followed, in process step b), by the recovery of one or more pure silicon compounds of the formula (Ia) from the resulting phase, especially a distillative workup in order to remove a reaction product formed, a silicon compound of the general formula (Ia). Surprisingly, the silicon compound can be isolated in high purity and also ultrahigh purity. A silicon compound of the formula (Ia) has a high purity when impurities are present only in the ppb range; ultrahigh purity is understood to mean impurities in the ppt range and lower.

It has been found that, surprisingly, by a treatment of a silicon compound which contains hydrogen, organyl and/or halogen and is of the following general formula (IIa) by means of nonthermal plasma, it is possible to obtain dimeric and/or trimeric silicon compounds of the general formula (Ia). These compounds are formed highly selectively, especially without significant contamination by-products, in the nonthermal plasma.

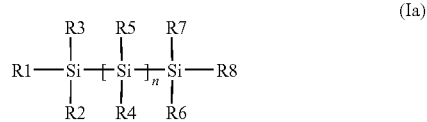

The R1 to R8 radicals of the silicon compound of the general formula (Ia) are each hydrogen and/or halogen, where the halogen is selected from fluorine, chlorine, bromine and/or iodine, with the proviso that at least one of the R1 to R8 radicals is a halogen atom, where R1 to R8 may denote identical or different radicals and the numerator n=0 or 1. Particularly preferred compounds are hexachlorodisilane where n=0 and octachlorotrisilane where n=1, and the R1 to R8 radicals in both compounds are chlorine. Further preferred compounds have a numerator n=0 or 1, where the R1 to R8 radicals are all a halogen atom. In appropriate compounds, the R1 to R8 radicals are halogen and hydrogen atoms.

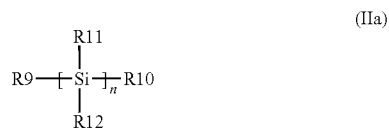

(IIa)

The R9 to R12 radicals of the silicon compound of the general formula (IIa) are each hydrogen, organyl, where the organyl comprises a linear, branched and/or cyclic alkyl having 1 to 18 carbon atoms, linear, branched and/or cyclic alkenyl having 2 to 8 carbon atoms, unsubstituted or substituted aryl and/or corresponding benzyl, the organyl especially containing hydrogen, or halogen, where the halogen is selected from fluorine, chlorine, bromine and/or iodine, and where the R9 to R12 radicals may denote identical or different radicals and the numerator n=1 or 2. The particularly preferred compound, silicon tetrachloride, has a numerator of n=1 and chlorine as R9 to R12 radicals. In further preferred embodiments, the numerator n=1 or 2 and the R9 to R12 radicals are each halogen atoms. Also appropriate are compounds with halogen and organyl radicals or hydrogen atoms; or halogen and organyl radicals. The compounds of the general formula (Ia) serve as a starting substance and as a matrix in the process.

It has been found in accordance with the invention that, by a treatment of the silicon compounds which contain hydrogen, organyl and/or halogen and are of the following general formula (IIa), in the presence of one or optionally more than one further silicon compound of the general formula (IIIa), the compounds of the formulae (IIa) and (IIIa) especially being nonidentical, by means of nonthermal plasma, it is possible to obtain dimeric and/or trimeric silicon compounds of the general formula (Ia). The silicon compounds (IIa) and (IIIa) are treated in a nonthermal plasma especially without addition of a reducing agent, for example hydrogen.

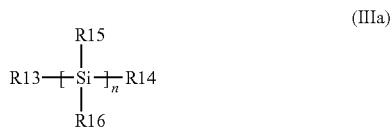

(IIIa)

Silicon compounds of the general formula (IIIa) have, as R13 to R16 radicals, hydrogen, organyl, where the organyl comprises a linear, branched and/or cyclic alkyl having 1 to 18 carbon atoms, linear, branched and/or cyclic alkenyl having 2 to 8 carbon atoms, unsubstituted or substituted aryl and/or corresponding benzyl, the organyl especially containing hydrogen, or the radicals contain halogen, where the halogen is selected from fluorine, chlorine, bromine and/or iodine and where the R13 to R15 radicals may be identical or different and the numerator n=1 or 2, where the numerator n=1 is preferred, especially with the proviso that it is a hydrogen-containing compound. The formation of a dimeric silicon compound of the formula (Ia) surprisingly proceeds highly selectively. By-products are formed only to a minor degree.

Hydrogen-containing compounds include silicon compounds which contain hydrogen bonded to silicon and/or hydrogen to an organyl radical.

Particularly preferred compounds of the formula (IIIa) have a numerator of n=1 and, on the R13 to R16 radicals, chlorine and hydrogen or an alkyl radical, for example methyl. Examples of these compounds are trichlorosilane ($HSiCl_3$), dichlorosilane ($H_2SiCl_2$), monochlorosilane ($H_3SiCl$), monosilane ($SiH_4$) and methyltrichlorosilane ($MeSiCl_3$), and also dimethyldichlorosilane ($Me_2SiCl_2$). In further appropriate compounds, the numerator n=1 or 2, where the R13, R15 and R16 radicals are each halogen atoms and R14 is a hydrogen or an alkyl radical. When mixtures of silicon compounds of the formulae (IIa) and (IIIa) with a numerator of n=1 and n=2 are used, dimeric and/or trimeric silicon compounds of the formula (Ia) can be obtained by equilibration reactions.

In the process for preparing the silicon compound of the formula (Ia), the silicon compound of the general formula (IIa) where n=1 does not correspond to any of the following compounds $H_mSiX_{4-m}$ (X=F, Cl, Br, I; m=0-3) when the silicon compound of the general formula (IIIa) where n=1 is one of the compounds $H_mSiX_{4-m}$ (X=F, Cl, Br, I; m=0-3).

According to the invention, a perhalogenated compound of the formula (IIa) is reacted with one or more hydrogen-containing compounds of the formula (IIIa) without addition of a reducing agent in a nonthermal plasma to give a silicon compound of the formula (Ia), and the pure, especially high-purity, silicon compound of the formula (Ia) is obtained.

In a particularly preferred embodiment, dimeric and/or trimeric silicon compounds of the formula (Ia) are obtained by reacting silicon tetrachloride ($SiCl_4$) of the formula (IIa) with one or further hydrogen-containing silicon compounds of the formula (IIIa) in nonthermal plasma.

The silicon tetrachloride here is simultaneously reactant and matrix, and so it is typically added in an excess relative to the hydrogen-containing compound. A considerable advantage of the process according to the invention is that the addition of a reducing agent, such as hydrogen, can be dispensed with. In contrast to the known prior art processes, a mobile homogeneous reaction mixture is obtained. Moreover, no precipitates or oily substances form; more particularly, the reaction mixture does not solidify in the course of storage at room temperature. The dimeric compound of the formula (Ia), especially the hexachlorodisilane, is advantageously formed highly selectively, such that almost exclusively the dimeric chlorinated silicon compound is present in the liquid reaction product. A further product or by-product may be octachlorotrisilane. This leads to a significantly simplified separation of the reaction product. This makes it possible to provide the products in a controlled manner in pure and highly pure form, especially after a distillative purification. The silicon compounds prepared by the process according to the invention are suitable for use in the semiconductor industry or pharmaceutical industry.

In the synthesis of the chlorosilanes, for example tetrachlorosilane ($SiCl_4$) and trichlorosilane ($HSiCl_3$), they are obtained as mixtures of the two compounds with further silicon compounds, such as alkylchlorosilanes. Typically, methylchlorosilane is present in the mixture. It is a great advantage of the process according to the invention that these mixtures can be supplied to the plasma without preceding purification by distillative removal of the individual compounds. Instead, for a given silane compound, the content of hydrogen-containing silane compounds can be increased by metering in trichlorosilane and/or methylchlorosilane.

Unconverted reactants of the general formula (IIa) and if appropriate (IIIa) are fed back to the nonthermal plasma if required. For complete conversion of the reactants to the compound of the general formula (Ia), a cycle mode with 1 to 100 cycles can be used; preference is given to a small number of 1 to 5 cycles; preferably only one cycle is passed through. The silicon compounds of the general formula (Ia) which are obtained in the nonthermal plasma by means of the reaction are already present in pure form in the resulting phase, from which they can be obtained in high purity; more particularly, they are subjected to a distillative workup. In this way, for example, hexachlorodisilane can be isolated in ultrahigh purity from the remaining reaction products and reactants; see FIG. 1. In the $^{29}$Si NMR spectrum, aside from the signal of the hexachlorodisilane ($\delta$=7.4±0.1 ppm, DMSO), no further compounds are detectable. The contamination of the silicon compounds with other metal compounds is at least in the ppb range down to the ppt range, preferably in the ppt range.

The nonthermal plasma is obtained in a plasma reactor in which a plasmatic conversion of matter is induced and is based on anisothermal plasmas. For these plasmas, a high electron temperature $T_e$ of $\geq 10^4$ K and relatively low gas temperature $T_G \leq 10^3$ K are characteristic. The activation energy needed for the chemical processes is provided predominantly through electron impacts (plasmatic conversion of matter). Typical nonthermal plasmas can be obtained, for example, by glow discharge, HF discharge, hollow cathode discharge or corona discharge. The working pressure at which the inventive plasma treatment is performed is in the range from 1 to 1000 $mbar_{abs}$, preferably 1 to 800 $mbar_{abs}$, more preferably 100 to 500 $mbar_{abs}$, especially 200 to 500 $mbar_{abs}$, the phase to be treated preferably being adjusted to a temperature of −40° C. to 200° C., more preferably to 20 to 80° C., most preferably to 40 to 60° C. In the case of germanium compounds, the corresponding temperature may also be higher.

For a definition of nonthermal plasma and of homogeneous plasma catalysis, reference is made to the relevant technical literature, for example to "Plasmatechnik: Grundlagen and Anwendungen—Eine Einführung [Plasma technology: fundamentals and applications—an introduction]; collective of authors, Carl Hanser Verlag, Munich/Vienna; 1984, ISBN 3-446-13627-4".

In the inventive embodiment of the process, silicon tetrachloride ($SiCl_4$) is reacted with at least one further hydrogen-containing silicon compound of the formula (IIIa) in a plasma reactor for gas phase treatment, especially without addition of a reducing agent. Examples of silicon compounds of the formula (IIIa) include trichlorosilane, dichlorosilane, monochlorosilane, monosilane, methyltrichlorosilane, dimethyl-dichlorosilane, trimethylchlorosilane and/or propyl-trichlorosilane.

An alternative preferred embodiment envisages the reaction of silicon tetrachloride only with further hydrosilanes, such as trichlorosilane. Further preferred embodiments envisage the reaction of silicon tetrachloride only with silanes containing organyl groups; for example, methyltrichlorosilane is added to the tetrachlorosilane and then supplied to the reactor. Both alternative embodiments proceed especially without addition of a reducing agent.

Generally preferred process variants envisage a reaction of the silicon tetrachloride with silicon compounds of the general formula (IIIa), in which case, for example, hydrosilanes such as trichlorosilane and/or alkylated silicon compounds such as methyltrichlorosilane are subjected to a nonthermal plasma treatment, especially without addition of a reducing agent.

A further advantage of the processes mentioned is that the addition of expensive inert noble gases can be dispensed with. Alternatively, an entraining gas, preferably an inert gas under pressure, such as nitrogen, argon, another noble gas or mixtures thereof can be added.

The silicon compound of the general formula (Ia) formed in process step a) is enriched in a collecting vessel of the apparatus for performing the process, for example in the bottom of the apparatus, and sent to a distillative workup. Process steps a) and/or b) can be performed batchwise or continuously. Of particular economic interest is a process regime in which process steps a) and b) are effected continuously. The compounds of the formula (IIa) and if appropriate of the formula (IIIa) are fed continuously to the plasma reactor for gas phase treatment. The higher-boiling reaction products are separated out of the phase which forms in a collecting vessel. It may be appropriate first to enrich the compound of the formula (Ia) in the collecting vessel at the start of the process, or else to feed unconverted compounds of the formula (IIa) and/or (IIIa) back into the reactor. This can be monitored by taking samples and analyzing them by means of FT-IR or NMR spectroscopy. Thus, the process can suitably also be monitored continuously ("online analysis"). As soon as the compound of the formula (Ia) has reached a sufficient concentration in the collecting vessel (bottom), the distillative workup to remove the silicon compound of the general formula (Ia) can be effected in continuous or batchwise mode. For a batchwise distillative workup, one column is sufficient for separation. To this end, the compound is withdrawn in high or ultrahigh purity at the top of a column with a sufficient number of separating stages. The required purity can be monitored by means of GC, IR, NMR, ICP-MS, or by resistivity measurement or GD-MS after deposition of the Si.

According to the invention, the continuous workup of the process products is effected in a column system with at least two columns, preferably in a system with at least 3 columns. In this way, for example, the hydrogen chloride gas (HCl) likewise formed in the reaction can be removed by means of a so-called low boiler column via the top, first column, and the mixture collected from the bottom can be separated into its constituents, by distillatively removing silicon tetrachloride ($SiCl_4$) at the top of a second column and hexachlorodisilane ($Si_2Cl_6$) at the top of a third column; if appropriate, a fourth column can be connected for removal of the octachlorotrisilane. In this way, the reaction mixture obtained from the plasma reactor can be separated by rectification, and the hexachlorodisilane or octachlorotrisilane reaction product can be obtained in the desired purity. The distillative workup of the silicon compound of the formula (Ia) can be effected either under standard pressure or under reduced or elevated pressure, especially at a pressure in the range from 1 to 1500 $mbar_{abs}$. Preferred pressures are in the range from 40 to 250 $mbar_{abs}$, especially in the range from 40 to 150 $mbar_{abs}$, preferably in the range from 40 to 100 $mbar_{abs}$. The top temperature of the column for distillative workup of the silicon compound of the formula (Ia) under reduced pressure has a top temperature in the range from 50 to 250° C.; more particularly, the vacuum is adjusted such that the temperature is in the range from 50 to 150° C., more preferably in the range from 50 to 110° C., during the isolation of the compound of the formula (Ia). The process products which are not very highly contaminated in any case can be isolated in very high to ultrahigh purity by the distillative workup. The corresponding temperatures for workup of the germanium compounds of the formula (Ib) may be increased somewhat.

The high-purity or ultrahigh-purity dimeric and/or trimeric silicon compounds of the general formula (Ia) prepared by the process according to the invention is suitable to a high degree for use in the preparation of silicon nitride, silicon oxynitride, silicon carbide, silicon oxycarbide or silicon oxide, especially for production of layers of these materials and for production of epitactic layers, preferably by low-temperature epitaxy. These layers can be produced, for example, by means of chemical vapor deposition (CVD). The high-purity or ultra-high-purity dimeric and/or trimeric silicon compounds of the general formula (Ia) prepared by the process according to the invention are preferably also suitable as a starting substance for the preparation of high-purity disilane ($Si_2H_6$) or trisilane ($Si_3H_8$).

In accordance with the general process, it is likewise possible to obtain high-purity germanium compounds of the general formula (Ib) from germanium compounds of the general formulae (IIb) and (IIIb). Dimeric and/or trimeric germanium compounds of the general formula (Ib)

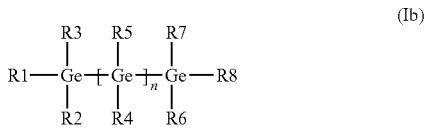
(Ib)

where R1 to R8 are each hydrogen and/or halogen, where the halogen is selected from chlorine, bromine and/or iodine, where R1 to R8 denote identical or different radicals in the formula (Ib), with the proviso that at least one of the R1 to R8 radicals is a halogen, and n=0 or 1, can be prepared by exposing a) a germanium compound of the general formula (IIb)

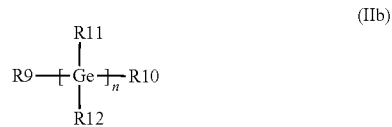
(IIb)

where R9 to R12 are each hydrogen, organyl, where the organyl comprises a linear, branched and/or cyclic alkyl having 1 to 18 carbon atoms, linear, branched and/or cyclic alkenyl having 2 to 8 carbon atoms, unsubstituted or substituted aryl and/or corresponding benzyl, and/or halogen, and the halogen is selected from chlorine, bromine and/or iodine, where R9 to R12 denote identical or different radicals in the formula (IIb) and n=1 or 2, or the germanium compound of the formula (IIb), in the presence of one or more compounds of the general formula (IIIb)

(IIIb)

where R13 to R16 are each hydrogen, organyl, where the organyl comprises a linear, branched and/or cyclic alkyl having 1 to 18 carbon atoms, linear, branched and/or cyclic alkenyl having 2 to 8 carbon atoms, unsubstituted or substituted aryl and/or corresponding benzyl, and/or halogen, and the halogen is selected from chlorine, bromine and/or iodine, where R13 to R16 denote identical or different radicals of the formula (IIIb) and n=1 or 2, especially with the proviso that it is a hydrogen-containing compound, to an nonthermal plasma and b) obtaining one or more pure germanium compounds of the general formula (Ib) from the resulting phase. More particularly, the phase is subjected to a distillative workup in process step b).

All abovementioned processes and embodiments of the processes for the silicon compounds can be applied to germanium compounds of the general formulae (IIb) and (IIIb) for preparation of germanium compounds of the general formula (Ib), and so it is also possible by the process according to the invention to prepare high-purity germanium compounds, especially $Ge_2Cl_6$ and $Ge_3Cl_8$. According to the invention, useful reactants here include perhalogenated germanium compounds, especially germanium tetrachloride, germanium tetrafluoride or mixed halogen compounds, which additionally contain organyl groups and/or hydrogen, as compounds of the formula (IIb) and hydrogen-containing compounds of the general formula (IIIb). These compounds can, especially after purification, be used to dope semiconductors, especially silicon, or to produce nanostructures.

The inventive apparatus comprises a reactor for generating the nonthermal plasma, a collecting vessel and a column system for distillative workup, in which case the column system for the continuous process regime comprises at least two columns, especially at least 3 columns. In an appropriate variant, the column system may comprise four columns. In the batchwise process regime, one column is sufficient. The columns are, for example, rectification columns.

The apparatus is suitable especially for performing the process according to the invention, in which case the reaction of the silicon compound of the formula (IIa) with optionally one or more compounds of the formula (IIIa) in process step a) is effected in the reactor. According to the boiling point, the reaction products can be enriched in a collecting vessel assigned to the reactor or else directly partly be removed directly from the apparatus in process step b) via a column system assigned to the apparatus.

Use of the inventive column system in the continuous process regime allows, for example, hydrogen chloride gas to be drawn off directly from the apparatus via a low boiler column at the top of the first column, then unconverted tetrachlorosilane can be withdrawn at the top of the second column and the higher-boiling reaction products of the general formula (Ia) at the top of the third column. When a plurality of higher-boiling reaction products of the formula (Ia) are isolated, a fourth column may be assigned.

Moreover, in the apparatus, in addition to the reactor, it is also possible to use one or more further reactors which are connected in series or parallel. According to the invention, at least one reactor of the apparatus is an ozonizer. A great advantage consists in the alternatively possible use of commercial ozonizers, such that the capital costs can be lowered significantly. The reactors of the invention are appropriately equipped with glass tubes, especially with quartz glass tubes, in which case the tubes are preferably arranged in parallel or coaxially and spaced apart by means of spacers of inert material. Suitable inert materials are especially Teflon or glass. It is known that the electron energy absorbed for the plasma discharge "E" depends on the product of pressure "p" and electron distance "d" (p·d). For the process according to the invention, the product of electron distance and pressure is generally in the range from 0.001 to 300 mm·bar, preferably from 0.05 to 100 mm·bar, more preferably 0.08 to 0.3 mm·bar, especially 0.1 to 0.2 mm·bar. The discharge can be induced by means of various kinds of alternating voltages or pulsed voltages of 1 to $10^6$ V. Equally, the curved profile of the voltage may, among other profiles, be rectangular, trapezoidal, pulsed, or be composed of fragments of individual profiles with time. Pulsed induction voltages are particularly suitable; they enable simultaneous formation of the discharge within the entire discharge space of the reactor. The pulse duration in the case of pulsed operation is guided by the gas system; it is preferably in the range from 10 ns to 1 ms. Preferred voltage amplitudes are 10 Vp to 100 kVp, preferably 100 Vp to 10 Vp, especially 50 to 5 Vp, in a microsystem. The frequency of the alternating voltage may be in the range from 10 MHz to 10 ns pulses (duty ratio 10:1) down to low frequencies in the range from 10 to 0.01 Hz. For example, an alternating voltage with a frequency of 1.9 kHz and an amplitude of 35 kV "peak to peak" can be applied on the reactor. The power input is about 40 W.

The silicon compounds of the formula (Ia) or germanium compounds of the formula (Ib) prepared by the process according to the invention are suitable for use in the semiconductor industry or pharmaceutical industry, since they have impurities only in the ppb range, preferably in the ppt range or lower. The compounds can be prepared in high and ultrahigh purity, because the compounds are formed surprisingly selectively in the process according to the invention and hence only few by-products in small amounts disrupt the workup of the process products.

The silicon compounds of the formula (Ia) prepared in accordance with the invention are therefore suitable for preparing silicon nitride, silicon oxynitride, silicon carbide, silicon oxycarbide or silicon oxide, especially for producing layers of silicon nitride, silicon oxynitride, silicon carbide, silicon oxycarbide or silicon oxide. In addition to hexachlorodisilane and/or octachlorotrisilane, it is appropriately also possible to use all further silicon compounds of the formula (Ia) to prepare the abovementioned layers. It is likewise possible to use the silicon compounds of the general formula (Ia) prepared in accordance with the invention, especially hexachlorodisilane and octachlorotrisilane, as a starting substance for preparing disilane or trisilane.

The example which follows illustrates the process according to the invention in detail without limiting the invention to this example.

EXAMPLE 1

Methyltrichlorosilane ($MeSiCl_3$)-enriched silicon tetrachloride ($SiCl_4$), silicon tetrachloride preferably being present in excess, is evaporated continuously and conducted into a nonthermal plasma of a gas discharge zone of a quartz glass reactor. The gas phase is conducted through the reactor at approximately 250 ml/h. While the gas phase flows through the reactor, an alternating voltage with a frequency of 1.9 kHz and an amplitude of 35 kV "peak to peak" is applied. The power input into the reactor is about 40 W. The operating pressure is set to about 300 mbar. After passing through the reactor, the reaction mixture is collected in liquid form in a collecting vessel. The gas chromatogram of the reaction mixture exhibits only one signal for high molecular weight silicon compounds and can be assigned to hexachlorodisilane. The distillation is effected batchwise in a distillation apparatus with a 50 cm column with Sulzer metal packing. At a bottom temperature of about 70° C. and a pressure of 750 $mbar_{abs}$, silicon tetrachloride is distilled off at a top temperature of about 50° C. Subsequently, the pressure is lowered to about 65 $mbar_{abs}$ and pure hexachlorodisilane is distilled off at a bottom temperature around 80° C. The top temperature is around 70° C. The content of metallic impurities corresponds to the detection limit in ICP-MS. The $^{29}Si$ NMR spectrum exhibits only one signal for hexachlorodisilane at −7.4 ppm; see FIG. 1.

The invention is illustrated in detail below by the working example shown in the FIGURE. It shows:

FIG. 1: 99.34 MHz $^{29}Si$ NMR spectrum of hexachlorodisilane in DMSO, prepared by the process according to the invention.

The invention claimed is:
1. A process, comprising:
reacting, in a nonthermal plasma, a silicon compound represented by formula (IIa) or a germanium compound represented by formula (IIb)

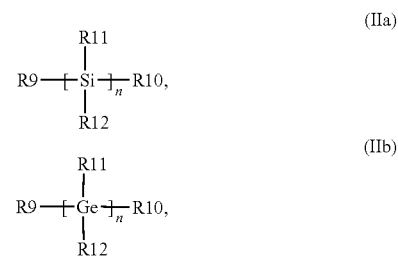

to obtain a silicon compound represented by formula (Ia) or a germanium compound represented by formula (Ib)

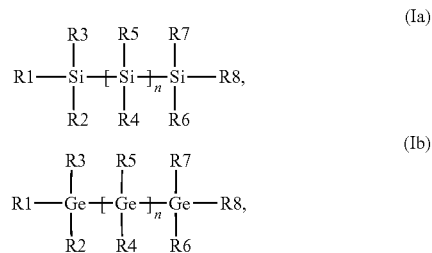

and, thereafter
recovering said compound represented by formula (Ia) or said compound represented by formula (Ib) from a phase that comprises said compound represented by formula (Ia) or said compound represented by formula (Ib),
wherein
each R1 to R8 radical is independently a hydrogen or a halogen selected from the group consisting of chlorine, bromine and iodine, with the proviso that at least one of the R1 to R8 radicals is a halogen, and n=0 or 1,
each R9 to R12 is independently a hydrogen; an organyl, where the organyl comprises a linear, branched or cyclic alkyl having 1 to 18 carbon atoms, linear, branched or cyclic alkenyl having 2 to 8 carbon atoms, unsubstituted or substituted aryl and/or corresponding benzyl; or a halogen selected from the group consisting of chlorine, bromine and iodine, and n=1 or 2,
said reacting of the silicon compound of formula (IIa) is carried out in the presence of at least one compound represented by formula (IIIa)

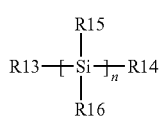
(IIIa)

or
and said reacting of the germanium compound of formula (IIb) is carried out in the presence of at least one compound represented by formula (IIIb)

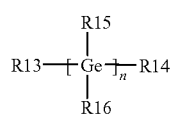
(IIIb)

where each R13 to R16 radical is independently a hydrogen; an organyl, where the organyl comprises a linear, branched or cyclic alkyl having 1 to 18 carbon atoms, linear, branched or cyclic alkenyl having 2 to 8 carbon atoms, unsubstituted or substituted aryl or corresponding benzyl; or a halogen selected from the group consisting of chlorine, bromine and iodine, n=1 or 2, and
wherein said reacting is carried out in the absence of a reducing agent.

2. The process as claimed in claim 1, wherein said recovering comprises distilling said compound represented by formula (Ia) or said compound represented formula (Ib) from the phase that comprises said compound represented by formula (Ia) or said compound represented by formula (Ib).

3. The process as claimed in claim 1, said process comprising reacting, in a nonthermal plasma, a silicon tetrachloride compound represented by formula (IIa), where R9 to R12=chlorine and n=1, and at least one further hydrogen-containing compound represented by formula (IIIa).

4. The process as claimed in claim 3, wherein
the hydrogen-containing compound represented by formula (IIIa) is at least one compound selected from the group consisting of methyltrichlorosilane, trichlorosilane, dichlorosilane, monochlorosilane, monosilane and dimethyldichlorosilane.

5. The process as claimed in claim 1, wherein at least one of said reacting and said recovering occurs continuously.

6. The process as claimed in claim 1, wherein
said reacting is carried out in an apparatus comprising a collecting vessel, and said
silicon compound represented by formula (Ia) obtained from said recovering is isolated to said collecting vessel.

7. The process as claimed in claim 1, wherein
said recovering is carried out in a continuous process regime and effected by distillation in a column system comprising at least two columns, and in a batchwise process regime with at least one column.

8. The process as claimed in claim 2, wherein
said distilling is carried out under standard pressure, reduced pressure or elevated pressure.

9. The process as claimed in claim 2, wherein
said distilling is carried out at a pressure in the range from 1 to 1500 $mbar_{abs}$.

10. The process as claimed in claim 2, wherein
said distilling is a distillation of the silicon compound of the formula (Ia), which occurs at top temperatures in the range from 40 to 250° C.

11. The process as claimed in claim 1, wherein
said reacting occurs at pressures in the range from 1 to 1000 $mbar_{abs}$.

12. The process as claimed in claim 1, wherein
the silicon compound represented by formula (Ia) is at least one of hexachlorodisilane and octachlorotrisilane.

13. The process as claimed in claim 1, wherein
the silicon compound of formula (Ia) has at least a purity in the ppb range.

14. The process according to claim 1, wherein at least one compound represented by Formula (IIIa), at least one compound represented by Formula (IIIb), or a combination thereof, is a hydrogen-containing compound.

15. The process as claimed in claim 1, wherein the silicon compound of formula (Ia) has a purity in the ppt range.

16. A process, comprising:
reacting, in a nonthermal plasma, a silicon compound represented by formula (IIa) or a germanium compound represented by formula (IIb)

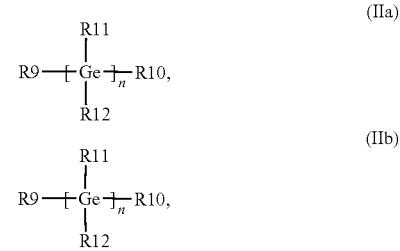

to obtain a silicon compound represented by formula (Ia) or a germanium compound represented by formula (Ib)

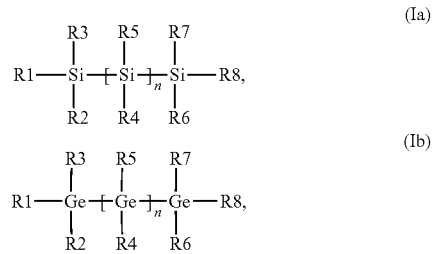

and, thereafter
recovering said compound represented by formula (Ia) or said compound represented by formula (Ib) from a phase that comprises said compound represented by formula (Ia) or said compound represented by formula (Ib),
wherein
each R1 to R8 radical is independently a hydrogen or a halogen selected from the group consisting of chlorine, bromine and iodine, with the proviso that at least one of the R1 to R8 radicals is a halogen, and n=0 or 1,
each R9 to R12 is independently a hydrogen; an organyl, where the organyl comprises a linear, branched or cyclic alkyl having 1 to 18 carbon atoms, linear, branched or cyclic alkenyl having 2 to 8 carbon atoms, unsubstituted or substituted aryl and/or corresponding benzyl; or a halogen selected from the group consisting of chlorine, bromine and iodine, and n=1 or 2,
said reacting of the silicon compound of formula (IIa) is carried out in the presence of at least one compound represented by formula (IIIa)

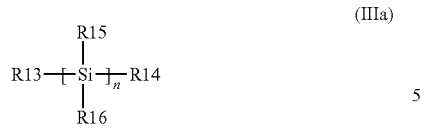

(IIIa)

or
and said reacting of the germanium compound of formula (IIb) is carried out in the presence of at least one compound represented by formula (IIIb)

(IIIb)

where each R13 to R16 radical is independently a hydrogen; an organyl, where the organyl comprises a linear, branched or cyclic alkyl having 1 to 18 carbon atoms, linear, branched or cyclic alkenyl having 2 to 8 carbon atoms, unsubstituted or substituted aryl or corresponding benzyl; or a halogen selected from the group consisting of chlorine, bromine and iodine, n=1 or 2, and wherein said reacting is carried out in the absence of hydrogen.

* * * * *